(12) United States Patent
Mizushima et al.

(10) Patent No.: US 10,446,364 B1
(45) Date of Patent: *Oct. 15, 2019

(54) FOCUSING MAGNET AND CHARGED PARTICLE IRRADIATION APPARATUS

(71) Applicant: B dot Medical Inc., Sakura-shi, Chiba (JP)

(72) Inventors: Kota Mizushima, Chiba (JP); Takuji Furukawa, Chiba (JP); Eri Takeshita, Chiba (JP); Yousuke Hara, Chiba (JP); Naoya Saotome, Chiba (JP); Yuichi Saraya, Chiba (JP); Ryohei Tansho, Chiba (JP)

(73) Assignee: B DOT MEDICAL INC., Sakura-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/359,414

(22) Filed: Mar. 20, 2019

Related U.S. Application Data

(63) Continuation of application No. 16/185,888, filed on Nov. 9, 2018.

(30) Foreign Application Priority Data

| Apr. 5, 2018 | (JP) | 2018-073303 |
| Jul. 2, 2018 | (JP) | 2018-125797 |

(51) Int. Cl.
*H01J 37/21* (2006.01)
*H01J 37/147* (2006.01)
(Continued)

(52) U.S. Cl.
CPC ............ *H01J 37/21* (2013.01); *A61N 5/1081* (2013.01); *H01J 37/141* (2013.01);
(Continued)

(58) Field of Classification Search
None
See application file for complete search history.

(56) References Cited

U.S. PATENT DOCUMENTS 6,327,339 B1 * 12/2001 Chung .................... G21K 5/04
250/505.1
8,389,949 B2  3/2013 Harada et al.
(Continued)

FOREIGN PATENT DOCUMENTS

EP     2308561 A1    4/2011
JP     60-20439 A    2/1985
(Continued)

OTHER PUBLICATIONS

Korean Notice of Allowance for Application No. 10-1974425, dated Apr. 11, 2019.

(Continued)

*Primary Examiner* — Andrew Smyth
(74) *Attorney, Agent, or Firm* — Birch, Stewart, Kolasch & Birch, LLP

(57) ABSTRACT

An embodiment of the invention is a focusing magnet including a coil pair arranged on both sides of a path of a charged particle beam. The coil pair generates an effective magnetic field region in which a magnetic field is oriented in a direction (z-axis) perpendicular to a traveling direction (x-axis) of a charged particle beam. In an xy-plane, an incident charged particle beam deflected at a deflection angle $\phi$ with respect to the x-axis at a deflection point Q is deflected by the effective magnetic field region, and irradiates an isocenter at an irradiation angle $\theta$ with respect to the x-axis; an arbitrary point P2 on a boundary on an exit side of the effective magnetic field region is at an equal distance $r_1$ from the isocenter; a point P1 on a boundary on an incident side of the effective magnetic field region and the point P2 are on a radius $r_2$ and an arc of a central angle ($\theta+\phi$);

(Continued)

and when a distance between the deflection point Q and the isocenter is L, a distance R between the deflection point Q and the point P1 satisfies a relational equation (4).

4 Claims, 13 Drawing Sheets

(51) Int. Cl.
  *A61N 5/10* (2006.01)
  *H01J 37/30* (2006.01)
  *H01J 37/141* (2006.01)
(52) U.S. Cl.
  CPC ...... *H01J 37/1475* (2013.01); *H01J 37/3005* (2013.01); *H01J 2237/049* (2013.01); *H01J 2237/141* (2013.01); *H01J 2237/24507* (2013.01)

(56) References Cited

U.S. PATENT DOCUMENTS

| | | |
|---|---|---|
| 8,487,278 B2 | 7/2013 | Balakin |
| 8,725,159 B2 | 5/2014 | Iwamura et al. |
| 2002/0030164 A1 | 3/2002 | Akiyama et al. |
| 2006/0106301 A1 | 5/2006 | Kats |
| 2010/0260317 A1 | 10/2010 | Chang et al. |
| 2011/0186746 A1* | 8/2011 | Drees ............... A61N 5/10 250/397 |
| 2013/0289330 A1 | 10/2013 | Haruna et al. |
| 2016/0193482 A1 | 7/2016 | Fahrig et al. |
| 2017/0252581 A1 | 9/2017 | Takizawa et al. |
| 2018/0064958 A1 | 3/2018 | Kobayashi et al. |
| 2018/0200539 A1* | 7/2018 | Amato ............... A61B 6/00 |

FOREIGN PATENT DOCUMENTS

| | | | |
|---|---|---|---|
| JP | 6-214100 A | | 8/1994 |
| JP | 06214100 A | * | 8/1994 |
| JP | 2836446 B2 | | 12/1998 |
| JP | 2002-113118 A | | 4/2002 |
| JP | 2004-97646 A | | 4/2004 |
| JP | 2009-119123 A | | 6/2009 |
| JP | 2011-142596 A | | 7/2011 |
| JP | 2011-523864 A | | 8/2011 |
| JP | 2012-11038 A | | 1/2012 |
| JP | 2012011038 A | * | 1/2012 |
| JP | 2013-505757 A | | 2/2013 |
| JP | 2013-240575 A | | 12/2013 |
| JP | 2017-153908 A | | 9/2017 |
| JP | 2017-153910 A | | 9/2017 |
| JP | 2018-38670 A | | 3/2018 |
| JP | 6364141 B1 | | 7/2018 |
| JP | 6387476 B1 | | 9/2018 |
| KR | 2000-0061395 A | | 10/2000 |
| KR | 20000061395 A | * | 10/2000 ............... G21K 5/04 |
| WO | WO 2010/143268 A1 | | 12/2010 |

OTHER PUBLICATIONS

Japanese Decision to Grant a Patent (including an English translation thereof) issued in the corresponding Japanese Patent Application No. 2018-073303 dated Jun. 19, 2018.

Japanese Decision to Grant a Patent (including an English translation thereof) issued in the corresponding Japanese Patent Application No. 2018-125797 dated Aug. 7, 2018.

Japanese Notice of Reasons for Rejection (including an English translation thereof) issued in the corresponding Japanese Patent Application No. 2018-073303 dated May 22, 2018.

* cited by examiner

FOCUSING MAGNET AND CHARGED PARTICLE IRRADIATION APPARATUS

CROSS-REFERENCE TO RELATED APPLICATION

This application is a Continuation application of co-pending application Ser. No. 16/185,888, filed on Nov. 9, 2018, which claims the benefit under 35 U.S.C. § 119(a) to Patent Application No. 2018-073303, filed in Japan on Apr. 5, 2018 and Patent Application No. 2018-125797, filed in Japan on Jul. 2, 2018, all of which are hereby expressly incorporated by reference into the present application.

FIELD OF THE INVENTION

The present invention relates to a focusing magnet and a charged particle irradiation apparatus using a focusing magnet.

BACKGROUND OF THE INVENTION

In conventional particle therapy, a charged particle beam accelerated to carry high energy irradiates a malignant tumor such as cancer to treat the tumor.

When a charged particle beam irradiates an object, energy (dose) is applied on the object along a charged particle beam path inside the object. When the dose is applied intensively on a limited area (target) inside the object, the charged particle beam is irradiated from various directions so that the charged particle beam overlaps with the target. This increases the dose concentration.

In the field of particle therapy, generally, a charged particle beam is irradiated from multiple directions to apply more dose to the target in the body, while suppressing exposure of normal tissues. Japanese Patent Laid-Open No. 2002-113118 discloses an apparatus for irradiating a charged particle beam from multiple directions to a target, in which multiple fixed irradiation ports are provided in a treatment room, and a device that varies the property of the charged particle beam is shared among the multiple fixed irradiation ports. Japanese Patent Laid-Open No. 60-20439 discloses an apparatus that irradiates a charged particle beam coming out from a single fixed irradiation port to a target from multiple directions, by rotating the target. Japanese Patent No. 2836446 discloses a rotary irradiation apparatus that rotates an entire charged particle beam transport device.

In the apparatus described in Japanese Patent Laid-Open No. 2002-113118, the number of directions in which the charged particle beam irradiates the target is the same as the number of the fixed irradiation ports. Hence, the directions (irradiation angle) in which the charged particle beam irradiates the target are not continuous. In addition, the same number of charged particle beam transport lines as the number of irradiation directions is required, which causes a problem of production cost and installation space. In the apparatus described in Japanese Patent Laid-Open No. 60-20439, the charged particle beam irradiates the target from various directions by rotating the patient. Hence, there are problems that this is physical and mental burdens on the rotating patient and that the tumor (target) tends to deform due to the rotation. In the apparatus described in Japanese Patent No. 2836446, although the charged particle beam can be irradiated continuously to the target, a large mechanism is required to integrally rotate the transport line and irradiation port of the charged particle beam. This causes a problem of manufacturing cost and installation space of such a mechanism.

BRIEF SUMMARY OF THE INVENTION

In view of the foregoing, an embodiment of the present invention aims to provide a focusing magnet capable of deflecting a charged particle beam incident from a relatively wide angle range and focusing the charged particle beam to the isocenter. Another embodiment of the present invention aims to provide a charged particle irradiation apparatus including the focusing magnet. Another embodiment of the present invention aims to provide a charged particle irradiation apparatus including the focusing magnet and an irradiation nozzle.

Embodiments of the present invention include [1] to [15]:

[1]

A focusing magnet comprising a coil pair arranged on both sides of a path of a charged particle beam, wherein:

when a current is input, the coil pair is configured to generate an effective magnetic field region in which a magnetic field is oriented in a direction (z-axis) perpendicular to a traveling direction (x-axis) of a charged particle beam, where an axis perpendicular to the x-axis and z-axis is assumed to be a y-axis;

in an xy-plane, a charged particle beam which has been deflected at a deflection angle $\phi$ with respect to the x-axis at a deflection point Q and incident on the effective magnetic field region is deflected by the effective magnetic field region, and irradiates an isocenter at an irradiation angle $\theta$ with respect to the x-axis, an arbitrary point P2 on a boundary on an exit side of the charged particle beam of the effective magnetic field region is at an equal distance $r_1$ from the isocenter, a point P1 on a boundary on an incident side of the charged particle beam of the effective magnetic field region and the point P2 are on a radius $r_2$ and an arc of a central angle $(\theta+\phi)$, and when a distance between the deflection point Q and the isocenter is L, a distance R between the deflection point Q and the point P1 satisfies the following relational equation (4):

$$R = \sqrt{L^2 + r_1^2 - 2L(r_1\cos\theta + r_2\sin\theta)} \qquad (4)$$

[2]

The focusing magnet according to [1], in which:

the focusing magnet includes two or more of the coil pairs;

the two or more coil pairs are arranged on both sides of a path of the charged particle beam and aligned in the y-axis direction;

of the two or more coil pairs, a selector unit is connected to a first coil pair and a second coil pair;

the selector unit is configured to supply current to any one of the first coil pair and the second coil pair; and the first coil pair and the second coil pair are configured such that the directions of the magnetic fields in generated effective magnetic field region are opposite to each other.

[3]

focusing magnet according to [1], in which the deflection point Q and the isocenter are on the x-axis.

[4]

A charged particle irradiation apparatus including:

an accelerator that generates a charged particle beam;

a bending magnet unit that deflects the charged particle beam from the accelerator at a deflection angle φ not smaller than 10 degrees at the deflection point Q;
the focusing magnet according to [1]; and
a power supply unit for supplying a current and exciting the focusing magnet.

[5]
The charged particle irradiation apparatus according to [4] further including a vacuum duct that connects the bending magnet unit and the focusing magnet, in which
the vacuum duct is formed into a fan shape on an xy-plane, and is configured to allow passage even of the charged particle beam deflected at the deflection angle φ not smaller than 10 degrees.

[6]
The charged particle irradiation apparatus according to [4] further including a drive unit that rotates the focusing magnet at a rotation angle co around the x-axis, in which
the charged particle beam irradiates the isocenter from a range of an arbitrary combination of the rotation angle co and the irradiation angle θ.

[7]
The charged particle irradiation apparatus according to [4], in which
the focusing magnet is arranged such that the longitudinal direction of the focusing magnet is tilted with respect to a floor surface of an irradiation room in which the charged particle irradiation apparatus is installed.

[8]
The charged particle irradiation apparatus according to [4] further including a quadrupole magnet provided on the upstream side of the bending magnet unit to adjust the shape of the charged particle beam.

[9]
The charged particle irradiation apparatus according to [8], in which an exciting current of the quadrupole magnet is controlled for each irradiation angle θ to adjust the shape of the charged particle beam for each irradiation angle θ.

[10]
The charged particle irradiation apparatus according to [4] further including:
a steering magnet unit provided on the upstream side of the bending magnet unit; and
a beam monitor unit provided on the exit side of the focusing magnet, in which
an exciting current of at least one of the bending magnet unit, the focusing magnet, and the steering magnet unit is used to perform feedback control, according to information on a position of the charged particle beam from the beam monitor unit.

[11]
The charged particle irradiation apparatus according to [4] further including imaging units provided on both sides of a target in the isocenter, in which
the imaging unit is configured to generate image information on the target before or during irradiation of the charged particle beam on the target.

[12]
A charged particle irradiation apparatus including:
a focusing magnet that deflects a charged particle beam to continuously vary an irradiation angle of the charged particle beam on an isocenter; and
an irradiation nozzle that moves continuously along the shape on an exit side of an effective magnetic field region of the focusing magnet, in which the charged particle beam exiting from the focusing magnet irradiates the isocenter through the irradiation nozzle.

[13]
A charged particle irradiation apparatus including:
the focusing magnet according to [1]; and
an irradiation nozzle that moves continuously along the shape on an exit side of an effective magnetic field region of the focusing magnet, in which
the charged particle beam exiting from the focusing magnet irradiates the isocenter through the irradiation nozzle.

[14]
The charged particle irradiation apparatus according to [13], in which:
the irradiation nozzle includes a scanning magnet that enables scanning of the charged particle beam within a prescribed range, and a beam monitor that monitors the charged particle beam; and
the charged particle irradiation apparatus further includes a scanning controller that controls the scanning magnet to scan the charged particle beam, on the basis of information from the beam monitor.

[15]
The charged particle irradiation apparatus according to [14], in which:
(i) the irradiation nozzle moves on a guide rail provided along the shape on an exit side of an effective magnetic field region of the focusing magnet, or
(ii) the irradiation nozzle is installed on a cover forming a part of the inner side of a wall surface of a treatment room, and when the cover moves continuously along the shape of the exit side of the effective magnetic field region of the focusing magnet, the irradiation nozzle moves continuously along the shape on the exit side of the effective magnetic field region of the focusing magnet.

The focusing magnet of an embodiment of the present invention can irradiate a charged particle beam to a target in a continuous direction (irradiation angle θ). The focusing magnet can focus the charged particle beam to the target even if the charged particle beam is incident from a relatively wide angle range. By using the focusing magnet, the burden on the patient and deformation of the target due to moving can be prevented or suppressed, without moving the target (patient). Additionally, in the focusing magnet, the effective magnetic field region is formed so that the irradiation angle θ at which the charged particle beam is focused to the target is determined according to the deflection angle φ. Hence, no enormous mechanism is required to physically move the focusing magnet, whereby the problem of production cost and installation space can be reduced accordingly.

DETAILED DESCRIPTION OF THE INVENTION

First Embodiment

A first embodiment of the present invention relates to a focusing magnet 10 that deflects a charged particle beam incident from a wide angle range, and focuses the charged particle beam to the isocenter.

Figure 1A:
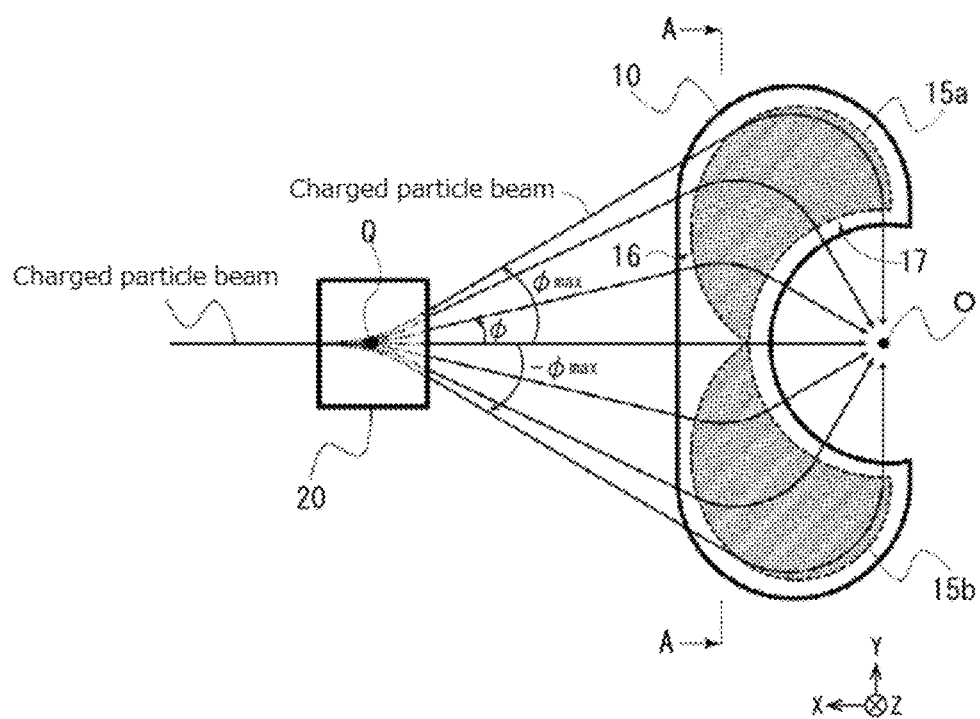
FIG. 1a is a schematic configuration diagram of a focusing magnet of an embodiment.

FIG. 1a is a schematic configuration diagram of the focusing magnet 10 of the embodiment. The traveling direction of the charged particle beam is indicated by the x-axis, the direction of a magnetic field generated by the focusing magnet 10 is indicated by the z-axis, and the direction perpendicular to the x-axis and z-axis is indicated by the y-axis. The focusing magnet 10 is configured to focus the charged particle beam incident from a wide range of deflection angle $\phi$ with respect to the x-axis on an xy-plane, to an isocenter O.

Figure 2:
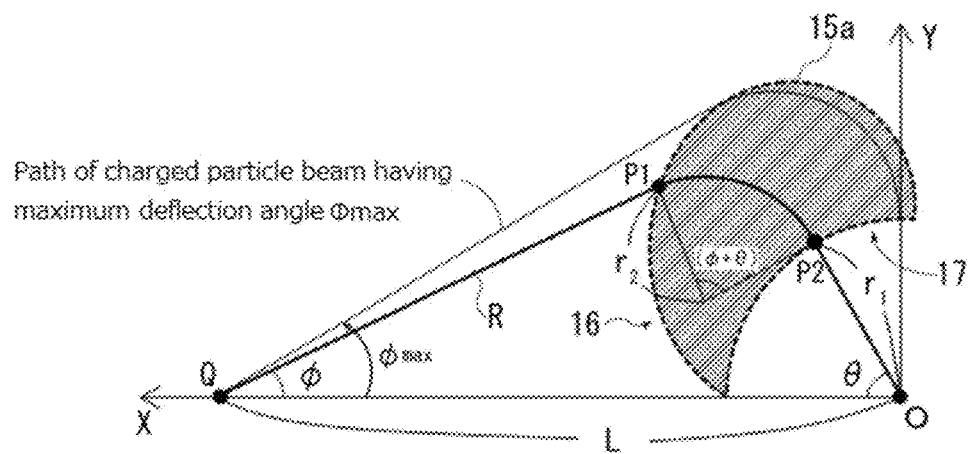
FIG. 2 is a diagram for describing how an effective magnetic field region of the embodiment is formed.

Here, although the isocenter O is the origin of the xyz-space and the upstream side (accelerator side) is regarded as the positive direction of the x-axis in the embodiment as shown in FIG. 2, the invention is not limited to this. The range of the deflection angle $\phi$ is within the range of −90 degrees to +90 degrees (not inclusive), and the range of the deflection angle may differ between positive (positive y-axis direction) and negative (negative y-axis direction). That is, later-mentioned effective magnetic field regions 15a, 15b may have an asymmetrical shape on the xy-plane. For example, the maximum deflection angle ($\phi=\phi$max) on the positive side may be 45 degrees, and the maximum deflection angle ($\phi=-\phi$max) on the negative side may be −30 degrees.

The focusing magnet 10 includes one or more coil pairs, and the coil pair is arranged in such a manner as to generate uniform magnetic fields (effective magnetic field regions 15a, 15b) oriented in a direction (z-axis direction in FIG. 1a) perpendicular to the traveling direction of the charged particle beam and the widening direction of the deflection angle $\phi$ of the charged particle beam, and on both sides of the path of the charged particle beam. An effective magnetic field region generated by one coil pair of the focusing magnet 10 has a falcate shape on the xy-plane as shown in FIG. 1a, and details will be described later. Note that since a gap (distance in z-axis direction) between opposite coil pairs through which the charged particle beam passes is sufficiently smaller than the widening range of the charged particle beam on the xy-plane, the widening of the charged particle beam in the z-axis direction will be ignored. The effective magnetic field regions 15a, 15b will collectively be referred to as an effective magnetic field region 15.

Figure 1B:
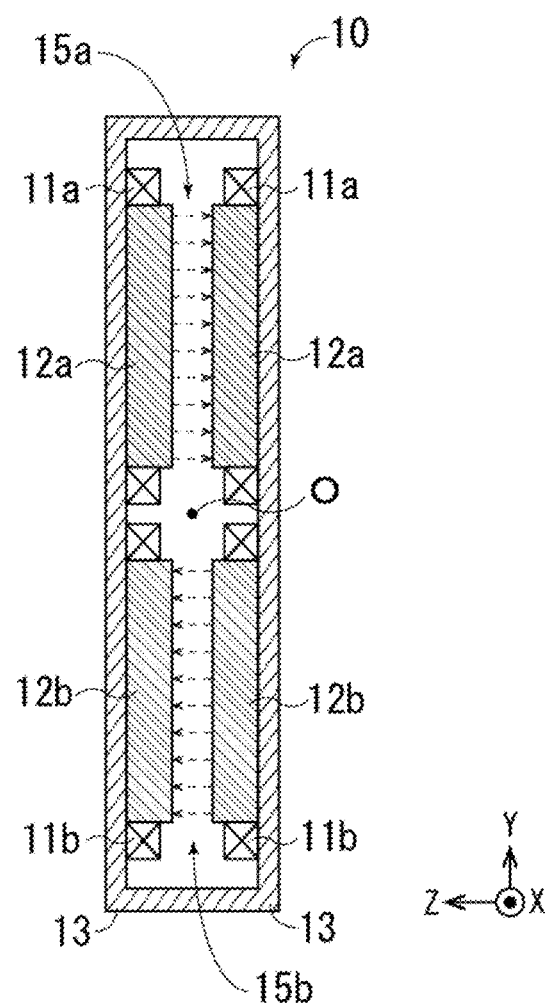
FIG. 1b is a cross-sectional view of the focusing magnet of the embodiment.

FIG. 1b is a cross-sectional view of the focusing magnet 10 taken along line A-A. In the embodiment, the focusing magnet 10 preferably includes at least two sets of coil pairs 11a, 11b. Magnetic poles 12a, 12b are embedded in the coils 11a, 11b, respectively, and a yoke 13 is connected to the magnetic poles 12a, 12b. A later-mentioned power supply unit (FIG. 3) is connected to the focusing magnet 10. The effective magnetic field regions 15a, 15b are formed by supplying a current (also referred to as exciting current) to the coil pair 11a, 11b from the power supply unit and exciting the focusing magnet 10. Note that the range of the effective magnetic field region 15a may differ from (asymmetrical to) the range of the effective magnetic field region 15b. For example, if the range of the positive (positive y-axis direction) deflection angle and the range of the negative (negative y-axis direction) deflection angle are asymmetrical, the effective magnetic field regions 15a, 15b may also be formed asymmetrically to reduce an unused effective magnetic field region.

The range of the deflection angle $\phi$ of the charged particle beam deflected by a bending magnet unit 20 and incident on the focusing magnet 10 is a range between the positive maximum deflection angle ($\phi=\phi$max) and the negative maximum deflection angle ($\phi=-\phi$max), where the positive maximum deflection angle $\phi$max is an angle not smaller than 10 degrees and smaller than 90 degrees, while the negative maximum deflection angle $-\phi$max is an angle larger than −90 degrees and not larger than −10 degrees. For example, the positive maximum deflection angle $\phi$max may be 10 degrees, 15 degrees, 20 degrees, 25 degrees, 30 degrees, 35 degrees, 40 degrees, 45 degrees, 50 degrees, 55 degrees, 60 degrees, 70 degrees, 80 degrees, or 85 degrees. The negative maximum deflection angle $-\phi$max may be, irrespective of the positive maximum deflection angle $\phi$max, −10 degrees, −15 degrees, −20 degrees, −25 degrees, −30 degrees, −35 degrees, −40 degrees, −45 degrees, −50 degrees, −55 degrees, −60 degrees, −70 degrees, −80 degrees, or −85 degrees. The deflection angle $\phi$ and a later-mentioned irradiation angle $\theta$ are angles of a charged particle beam path with respect to the x-axis on the xy-plane.

A charged particle beam incident within the range of the positive deflection angle ($\phi$=larger than 0 to $\phi$max) is deflected by the effective magnetic field region 15a of the first coil pair 11a, and irradiates the isocenter O. A charged particle beam incident within the range of the negative deflection angle ($\phi$=smaller than 0 to −$\phi$max) is deflected by the effective magnetic field region 15b of the second coil pair 11b, and irradiates the isocenter O. The directions of the magnetic fields in the effective magnetic field region 15a and the effective magnetic field region 15b are opposite to each other (positive and negative z-axis direction). Note that a charged particle beam incident on the focusing magnet 10 from the bending magnet unit 20 at the deflection angle $\phi=0$ passes through any one of or between the effective magnetic field regions 15a, 15b, and is focused to the isocenter O.

The deflection angle $\phi$ of the charged particle beam incident on the focusing magnet 10 is controlled by the bending magnet unit 20. The bending magnet unit 20 generates a magnetic field directed perpendicular (z-axis in FIG. 1a) to the traveling direction (x-axis in FIG. 1a) of the charged particle beam supplied from the accelerator (not shown), and includes a magnet that deflects the passing charged particle beam, and a controller (not shown) that controls the intensity and direction of the magnetic field. The bending magnet unit 20 controls the intensity and direction (z-axis direction) of the magnetic field to deflect the charged particle beam on the xy-plane, and delivers the charged particle beam deflected at the deflection angle ϕ at a deflection point Q to the focusing magnet 10. Here, the deflection point Q and the isocenter O are on the x-axis.

A vacuum duct (not shown) is provided between the accelerator and the bending magnet unit 20, and between the bending magnet unit 20 and the focusing magnet 10. The charged particle beam is transported through the vacuum duct, and therefore does not attenuate largely during transport.

A formula for forming the effective magnetic field region 15a of the focusing magnet 10 will be described with reference to FIG. 2. Note that since deflection of the charged particle beam in the z-axis direction is ignored, formation of the effective magnetic field region on the xy-plane will be described. Although the description is given of the effective magnetic field region 15a of the focusing magnet 10, the same applies for the effective magnetic field region 15b, and therefore the description thereof will be omitted.

First, the boundary of the effective magnetic field region 15a on an exit side 17 of the charged particle beam of the focusing magnet 10 is determined so as to be within an equal distance $r_1$ from the isocenter O. Next, the boundary of the effective magnetic field region 15a on an incident side 16 of the charged particle beam of the focusing magnet 10 is determined on the basis of the following relational equations (1) to (5), so that an incident charged particle beam deflects at the deflection angle ϕ in a virtual deflection point Q at a predetermined distance L from the isocenter O, and is focused to the isocenter O. Here, the virtual deflection point Q is a point obtained by assuming that the charged particle beam receives a kick of the deflection angle ϕ in an extremely short distance at the center of the bending magnet unit 20.

The charged particle beam transported at the deflection angle ϕ is incident from an arbitrary point P1 on the boundary of the effective magnetic field region 15a on the incident side 16, moves in a circular motion (central angle (ϕ+θ)) with a radius of curvature $r_2$ inside the effective magnetic field region 15a, exits from a point P2 on the boundary of the effective magnetic field region 15a on the exit side 17, and irradiates the isocenter O. That is, point P1 and point P2 are on a radius $r_2$ and an arc of the central angle (ϕ+θ).

Assume an x-y coordinate system where the isocenter O is the origin in an xy-plane. When an angle formed by a straight line connecting point P2 on the exit side 17 and the isocenter O and the x-axis is the irradiation angle θ, the coordinates (x, y) of point P1 on the incident side 16, the deflection angle 4), and a distance R between point Q and point P1 are obtained from the following relational equations (1) to (4):

$$x = r_1 \cos\theta + r_2(\sin\theta + \sin\phi) \quad (1)$$

$$y = r_1 \sin\theta - r_2(\cos\theta - \cos\phi) \quad (2)$$

$$\phi = \sin^{-1}\left(\frac{r_2}{\sqrt{R^2 + r_2^2}}\right) + \sin^{-1}\left(\frac{r_1\sin\theta - r_2\cos\theta}{\sqrt{R^2 + r_2^2}}\right) \quad (3)$$

$$R = L^2 + r_1^2 - 2L(r_1\cos\theta + r_2\sin\theta) \quad (4)$$

Here, a magnetic field having a uniform magnetic flux density B is generated in the effective magnetic field region 15a, and when a momentum (substantially dependent on accelerator) of the charged particle beam is p, and the charge is q, the radius of curvature $r_2$ of the charged particle beam deflected in the magnetic field is expressed by equation (5):

$$r_2 = \frac{p}{qB} \quad (5)$$

By adjusting the shape and arrangement of the coil pair 11a and the magnetic pole 12a of the focusing magnet 10 and adjusting the current applied to the coil pair 11a on the basis of the above relational equations (1) to (5), the shape of the boundary of the effective magnetic field region 15a can be adjusted. That is, the boundary is determined such that the distance between the arbitrary point P2 on the boundary of the effective magnetic field region 15a on the irradiation side 17 and the isocenter O is the equal distance $r_1$, the magnetic flux density B of the effective magnetic field region 15a is adjusted to determine $r_2$ from equation (5), and the boundary of the effective magnetic field region 15a on the incident side 16 is determined such that the distance R between the point P1 on the boundary of the effective magnetic field region 15a on the incident side 16 and the deflection point Q satisfies the relation of equation (4). The maximum value of 4) in equation (3) is the maximum deflection angle ϕmax. Note that although not limited to this, the arrangement of the deflection point Q, the focusing magnet 10, and the isocenter O is preferably adjusted so that the charged particle beam passing through the deflection point Q may focus to the isocenter O, even if the charged particle beam is not deflected by the focusing magnet 10 (ϕ=0). This simplifies the configuration of the apparatus.

The boundary of the effective magnetic field regions 15a, 15b of the focusing magnet 10 obtained in the above manner is an ideal shape for focusing the charged particle beam to the isocenter O. Note, however, that even if there is deviation from the ideal shape or non-uniformity in the magnetic field distribution in practice, the charged particle beam can be deflected toward the isocenter O, by previously fine-adjusting the excitation amount (magnetic flux density B) of the focusing magnet 10 for each deflection angle 4), storing the information in the power supply unit (not shown), and controlling the deflection angle 4) and the amount of current of the focusing magnet 10 so that they work in an interlocked manner. Moreover, if non-uniformity of the magnetic field distribution is predictable, the trajectory of the charged particle beam can be fine-adjusted by correcting the shape and arrangement of the coil pair 11a and the magnetic pole 12a of the focusing magnet 10.

Figure 3:
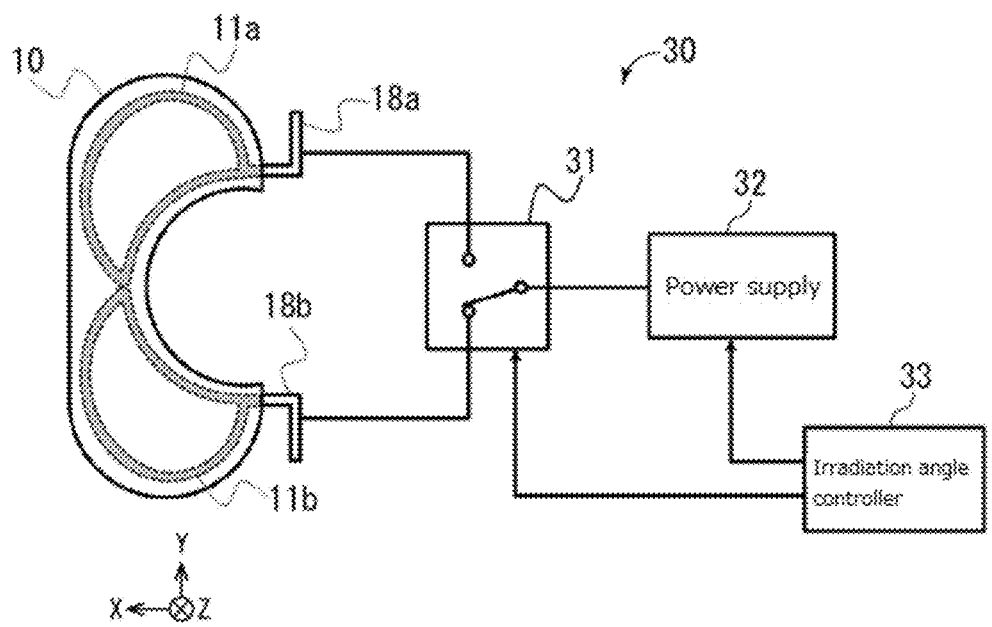
FIG. 3 is a schematic configuration diagram of a power supply unit of the embodiment.

FIG. 3 is a schematic configuration diagram of a power supply unit 30 that supplies a current to the focusing magnet 10. The power supply unit 30 includes a selector unit 31 connected to bus bars 18a, 18b which are current supply ends of the coil pairs 11a, 11b of the focusing magnet 10, a power supply 32 that applies a current to the coils 11a, 11b through the selector unit 31, and an irradiation angle controller 33 that controls the selector unit 31 and the power supply 32.

Since a charged particle beam basically passes through one of the coil pairs 11a, 11b, the power supply unit 30 is configured to switch the current (exciting current) supplied to the coil pairs 11a, 11b from the power supply 32 by the selector unit 31, and apply the current to one of the coil pairs 11a, 11b through which the charged particle beam passes.

The selector unit 31 and the power supply 32 are controlled by the irradiation angle controller 33. The irradiation angle controller 33 controls the power supply 32 to control the current applied to the coil pairs 11a, 11b, and controls the selector unit 31 to switch the coil pair 11a, 11b to which the current should be applied, depending on the energy of the charged particle beam and/or the deflection angle ϕ of the charged particle beam by the bending magnet unit 20. Since the irradiation angle controller 33 switches the current applied to the coil pair 11a, 11b by the selector unit 31, there are less coil pairs simultaneously connected to the power supply 32, and inductance and resistance can be reduced by the reduced number of coil pairs. Hence, the power supply capacity of the power supply 32 can be reduced.

The irradiation angle controller 33 may perform control in synchronization with the deflection direction (deflection angle ϕ) of the charged particle beam by the bending magnet unit 20. The irradiation angle controller 33 may periodically receive input of information on the deflection angle ϕ of the charged particle beam from the bending magnet unit 20, and control the selector unit 31 and the power supply 32 on the basis of the received information. Note that an energy and an excitation amount (current value of each coil pair 11a, 11b) of a charged particle beam corresponding to a deflection angle ϕ may be obtained beforehand, and be stored in association with the deflection angle ϕ in the irradiation angle controller 33. Then, the irradiation angle controller 33 may control the excitation amount depending on the deflection angle ϕ, by referring to the stored information.

Note that if the same amount of current applied to the coils 11a, 11b may be applied to the coil pairs 11a, 11b, that is, if the excitation amount is not varied among the deflection angles ϕ, the coil pair 11a and coil pair 11b may be connected in series, and a current may be applied to both coil pairs 11a, 11b from a single power supply 32. In this case, the power supply unit 30 may omit the selector unit 31.

The focusing magnet 10 of the embodiment can irradiate the charged particle beam to the target (isocenter O) in continuous directions (irradiation angles θ). The focusing magnet 10 can focus the charged particle beam to the target even if the charged particle beam is incident from a relatively wide angle range (e.g., maximum deflection angle of ±10 degrees to smaller than 90 degrees). Use of the focusing magnet 10 eliminates the need to move the target (patient), whereby the burden on the patient and deformation of the target due to moving can be prevented or suppressed, as compared to the conventional technique where the patient is moved. Additionally, in the focusing magnet 10, the effective magnetic field region is formed so that the irradiation angle θ at which the charged particle beam is focused to the target is determined according to the deflection angle ϕ. Hence, no enormous mechanism is required to physically move the focusing magnet, whereby the problem of production cost and installation space can be reduced accordingly.

Second Embodiment

A second embodiment of the present invention is related to a charged particle irradiation apparatus 100 using the focusing magnet 10 of the first embodiment.

Figure 4A:
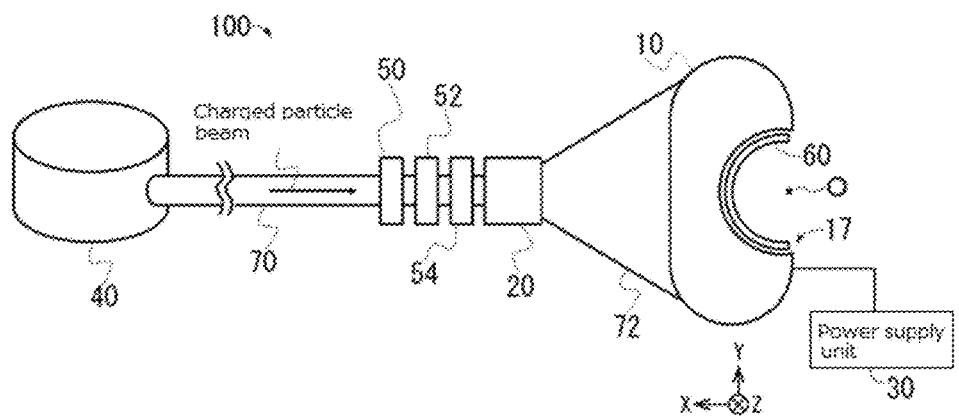
FIG. 4a is a schematic configuration diagram of a charged particle irradiation apparatus of the embodiment.
Figure 4B:
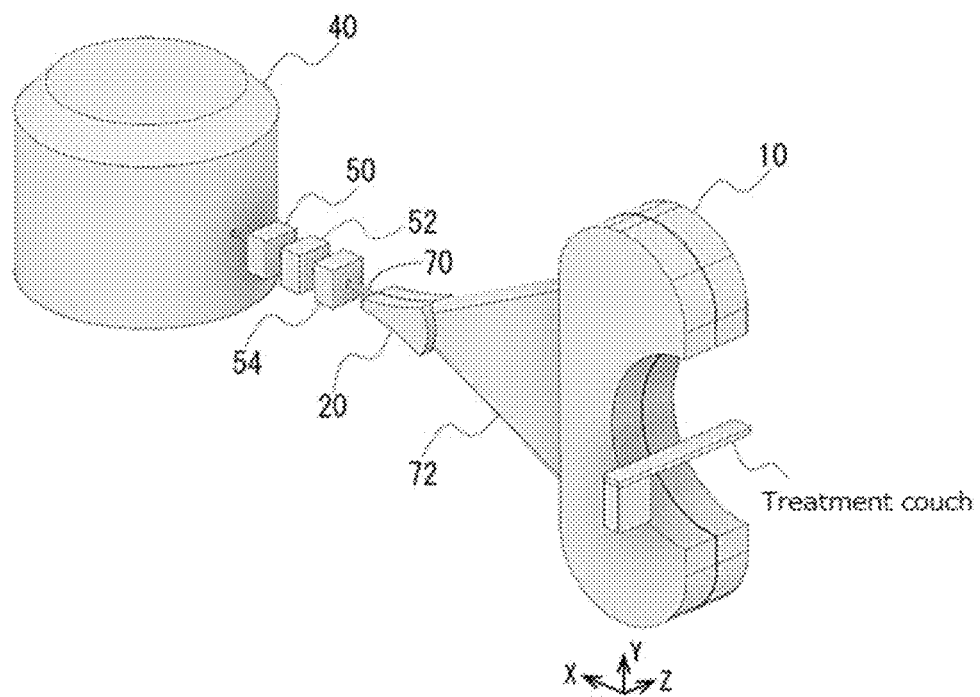
FIG. 4b is a schematic configuration diagram of the charged particle irradiation apparatus of the embodiment.

FIG. 4a is a schematic configuration diagram of the charged particle irradiation apparatus 100 of the embodiment, and FIG. 4b is a schematic perspective view of the charged particle irradiation apparatus 100 from an accelerator 40 on the upstream side to a focusing magnet 10 on the downstream side. The charged particle irradiation apparatus 100 has the focusing magnet 10, a bending magnet unit 20, a power supply unit 30, and the accelerator 40. In addition, the charged particle irradiation apparatus 100 may also have at least one or more components from among a beam slit unit 50, a quadrupole magnet unit 52, a steering magnet unit 54, and a beam monitor unit 60.

The accelerator 40 is a device that generates a charged particle beam, such as a synchrotron, a cyclotron, or a linear accelerator. The charged particle beam generated in the accelerator 40 is guided to the bending magnet unit 20, through a vacuum duct 70 whose internal space is kept in a vacuum state. If the charged particle irradiation apparatus 100 has the beam slit unit 50, the quadrupole magnet unit 52, and the steering magnet unit 54, each of the accelerator 40, the beam slit unit 50, the quadrupole magnet unit 52, the steering magnet unit 54, and the bending magnet unit 20 is connected by the vacuum duct 70.

The beam slit unit 50 includes a slit for adjusting the shape and/or dose of the charged particle beam, and a controller that controls the slit width. As will be described later, the controller may adjust the beam shape and/or dose by controlling the slit width on the basis of information from the beam monitor unit 60.

The quadrupole magnet unit 52 includes one or more quadrupole magnets for adjusting the shape of the charged particle beam, and a controller that controls the current applied to the quadrupole magnets to control the adjustment amount of the beam shape. As will be described later, the controller may adjust the beam shape by controlling the amount of current applied to the quadrupole magnets on the basis of information from the beam monitor unit 60. For example, the quadrupole magnet unit 52 includes at least two quadrupole magnets including a quadrupole magnet for adjusting the beam shape in the y-axis direction, and a quadrupole magnet for adjusting the beam shape in the z-axis direction.

The steering magnet unit 54 includes one or more magnets for fine-adjusting the position of the charged particle beam, and a controller that controls the current applied to the magnets to control the position of the charged particle beam. The controller may adjust the beam position by controlling the current applied to the magnets on the basis of information from the beam monitor unit 60.

Since the path of the charged particle beam from the bending magnet unit 20 to the isocenter O varies depending on the irradiation angle θ, the optical element that the charged particle beam receives also varies depending on the irradiation angle θ. Hence, the shape of the charged particle beam at the isocenter O sometimes varies depending on the irradiation angle θ. Against this background, the quadrupole magnet unit 52 provided on the upstream side of the focusing magnet 10 may control the current exciting the quadrupole magnet for each irradiation angle θ, and make adjustment so that an appropriate shape of the charged particle beam is formed at the isocenter O, for example. Moreover, the shape of the charged particle beam may be adjusted by the beam slit unit 50. In this case too, the slit width of the beam slit unit 50 may be controlled for each irradiation angle θ.

To maintain a high irradiation accuracy, the irradiation angle θ of the charged particle beam irradiating the isocenter O should preferably be controlled with high precision. However, the accuracy of the irradiation angle θ may decrease due to an alignment error of various units of the charged particle irradiation apparatus 100, or error in the magnetic field of various magnets. Accordingly, the beam monitor unit 60 that monitors the position of the charged particle beam may be provided on the exit side 17 of the focusing magnet 10. The beam monitor unit 60 may output information on the position and shape (e.g., beam size) of the charged particle beam to one or more components from among the beam slit unit 50, the quadrupole magnet unit 52, the steering magnet unit 54, the bending magnet unit 20, and an irradiation angle controller 33 of the power supply unit 30 of the focusing magnet 10, so that each component may perform feedback control.

For example, upon receipt of information from the beam monitor unit 60, the beam slit unit 50 adjusts the shape of the charged particle beam by controlling the slit width, the quadrupole magnet unit 52 adjusts the shape of the charged particle beam by controlling the exciting current applied to the quadrupole magnet, the steering magnet unit 54 adjusts the position of the charged particle beam by controlling the exciting current applied to the magnet, the bending magnet unit 20 adjusts the deflection angle $\phi$ of the delivered charged particle beam by controlling the exciting current applied to the magnet, or the irradiation angle controller 33 adjusts the irradiation angle $\theta$ of the charged particle beam irradiating the isocenter O.

Feedback control using the beam monitor unit 60 can further improve accuracy in irradiation to the isocenter O. Note that the relationship between the information (beam position and beam shape) to be fed back and the adjustment amount of each of the beam slit unit 50, the quadrupole magnet unit 52, the steering magnet unit 54, the bending magnet unit 20, and the irradiation angle controller 33 should preferably be obtained beforehand, and be pre-stored in each unit.

In the charged particle irradiation apparatus 100, a vacuum duct 72 for transporting the charged particle beam is provided between the bending magnet unit 20 and the focusing magnet 10. The vacuum duct 72 is a fan-shaped (xy-plane) vacuum duct that covers the range of the maximum deflection angle $\phi$ of the bending magnet unit 20. By forming the vacuum duct 72 on the xy-plane into a fan shape, the vacuum duct can be formed smaller than a rectangular type, whereby installation space can be reduced.

Figure 5:
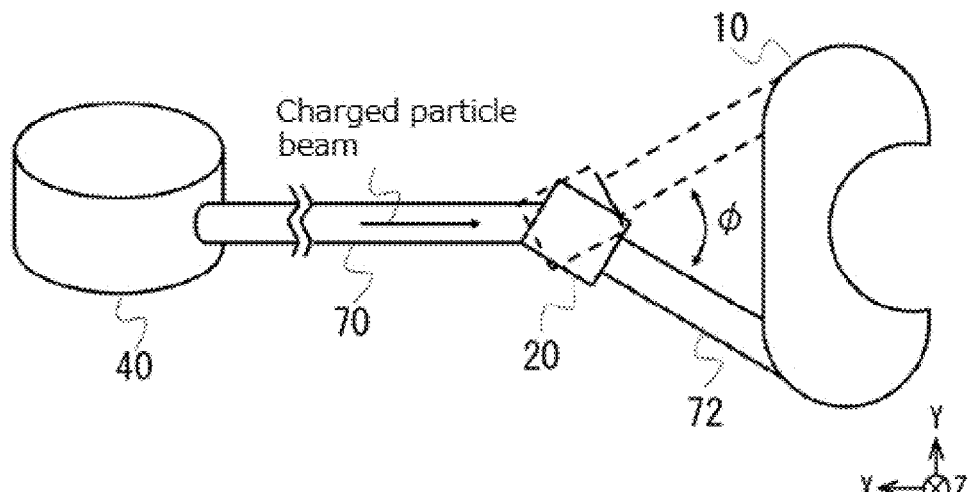
FIG. 5 is a schematic configuration diagram of the charged particle irradiation apparatus of the embodiment.

The vacuum duct 72 may be a tubular vacuum duct connected to an exit side of the bending magnet unit 20, as shown in FIG. 5. This structure allows the vacuum duct to be formed even smaller, and reduces installation space even more. In this case, a drive mechanism (not shown) may move the vacuum duct 72 on the xy-plane within the range between the positive maximum deflection angle ($\phi$max) and the negative maximum deflection angle ($-\phi$max), in association with the deflection angle $\phi$ of the bending magnet unit 20.

Figure 6:
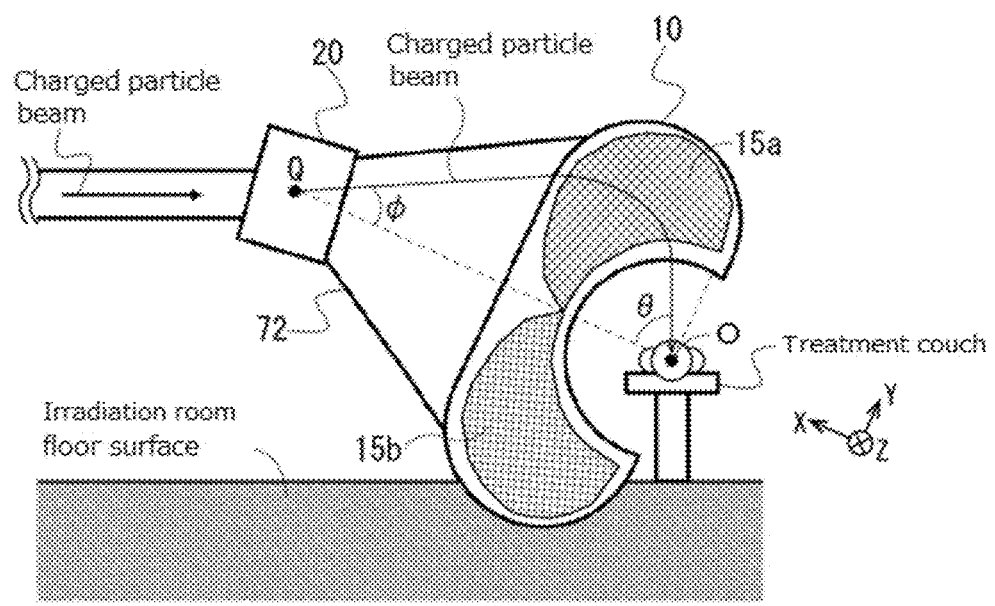
FIG. 6 is a schematic configuration diagram of the charged particle irradiation apparatus of the embodiment.

FIG. 6 is a schematic diagram showing how the charged particle irradiation apparatus 100 is used for particle therapy on a patient. In an irradiation room in which the charged particle irradiation apparatus 100 is installed to perform the particle therapy, the focusing magnet 10 may be arranged such that the longitudinal direction of the focusing magnet 10 is tilted with respect to the floor surface of the irradiation room. With this, the required ceiling height for installing the apparatus can be kept low. In this case, the traveling direction of the charged particle beam from the accelerator 40 and the isocenter O are not in the same straight line. Hence, assuming that a line connecting the deflection point Q of the charged particle beam in the bending magnet unit 20 and the isocenter O is an x-axis, effective magnetic field regions 15a, 15b can be formed on the basis of the relational equations (1) to (5) as described with reference to FIG. 2.

Third Embodiment

A third embodiment of the present invention relates to a charged particle irradiation apparatus 300 using a focusing magnet 200 that includes a single coil pair 11a.

Figure 7A:
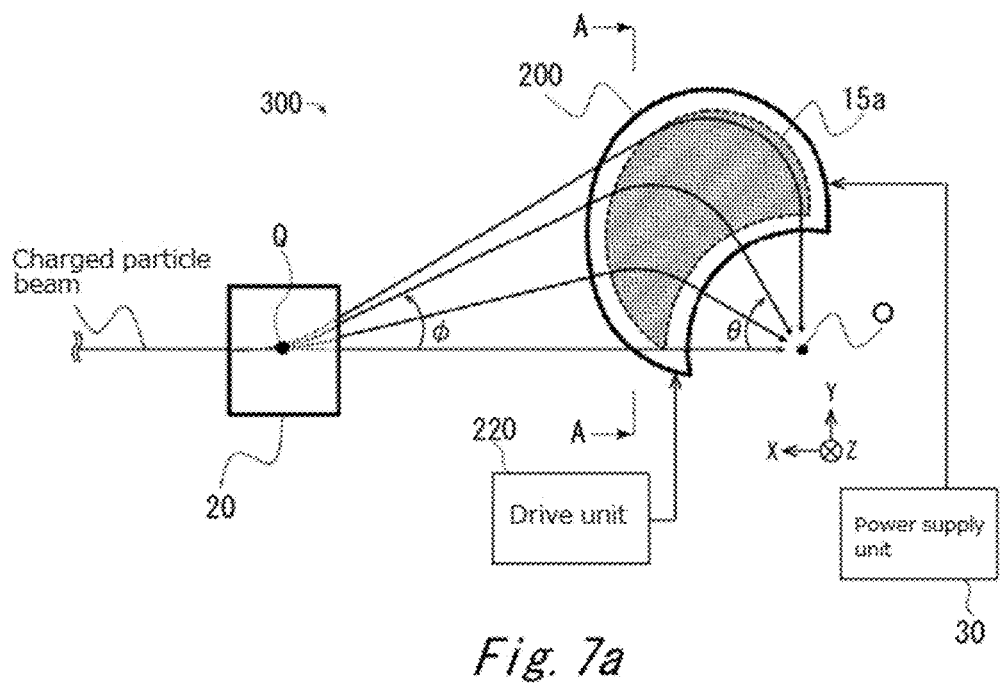
FIG. 7a is a schematic configuration diagram of the charged particle irradiation apparatus of the embodiment.
Figure 7B:
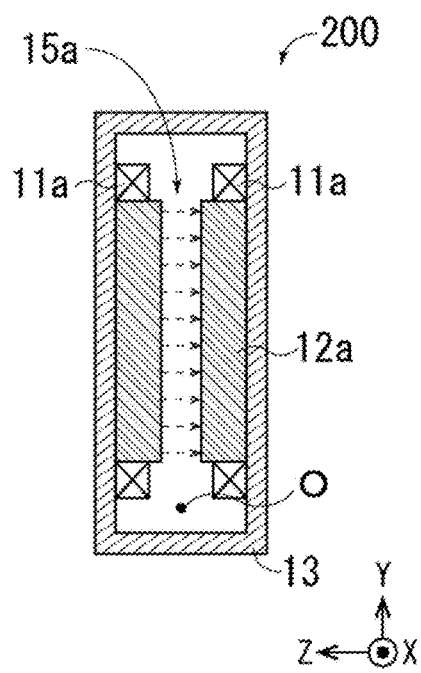
FIG. 7b is a schematic configuration diagram of the charged particle irradiation apparatus of the embodiment.

As shown in FIGS. 7a and 7b, the focusing magnet 200 of the embodiment includes the coil pair 11a, the magnetic pole 12a, and the yoke 13 of the focusing magnet 10 of the first embodiment. As compared to the focusing magnet 10 of the first embodiment, the focusing magnet 200 can reduce the volume of the yoke 13 forming the magnet by the amount of the coil pair 11b and the magnetic pole 12b, so that the weight of the focusing magnet 200 can also be reduced.

Although not shown, as in the case of the second embodiment, the charged particle irradiation apparatus 300 has a bending magnet unit 20, a power supply unit 30, and an accelerator 40, and also has a drive unit 220 that rotates the focusing magnet 200 around an x-axis passing through an isocenter O. The focusing magnet 200 and the bending magnet unit 20 are connected through a vacuum duct 240. Additionally, although not shown, the charged particle irradiation apparatus 300 may also have at least one or more components from among a beam slit unit 50, a quadrupole magnet unit 52, a steering magnet unit 54, and a beam monitor unit 60.

Figure 8:
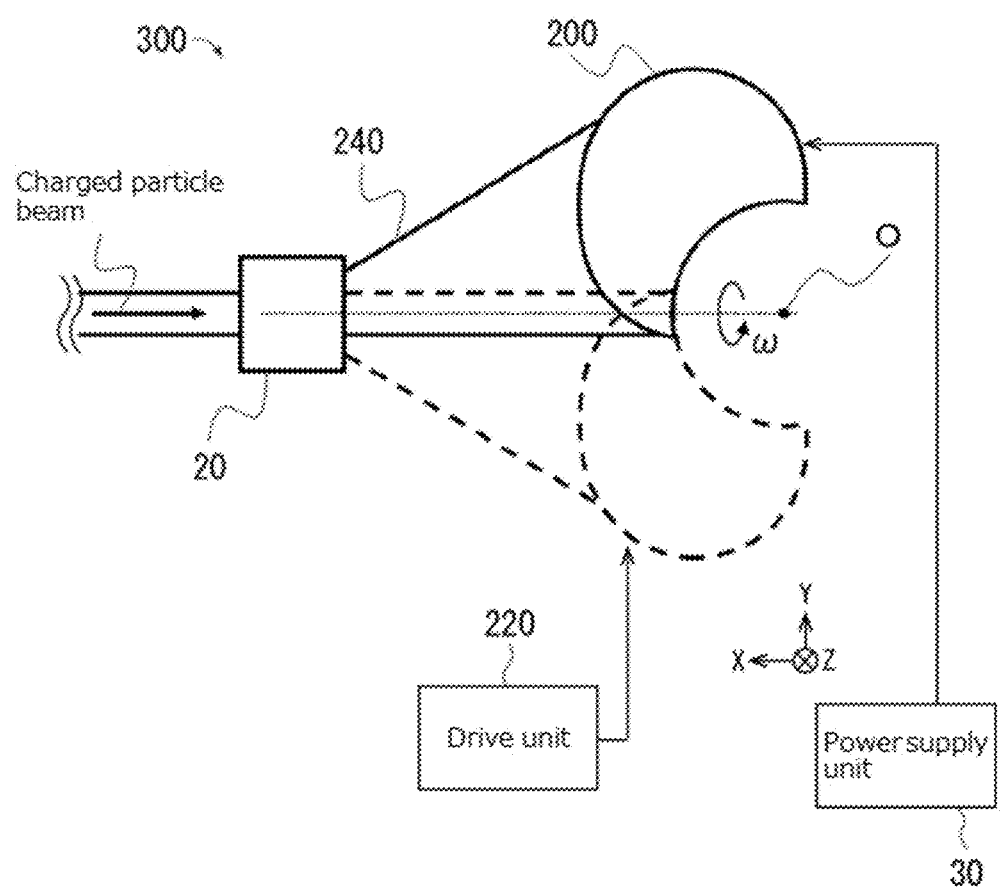
FIG. 8 is a schematic configuration diagram of the charged particle irradiation apparatus of the embodiment.

As shown in FIG. 8, in the charged particle irradiation apparatus 300, the charged particle beam can irradiate the isocenter O from a range of an arbitrary solid angle (combination of rotation angle $\omega$ around x-axis and irradiation angle $\theta$ on xy-plane), by rotating the focusing magnet 200 around the x-axis by the drive unit 220. Thus, the charged particle irradiation apparatus 300 enables particle therapy with three-dimensional and multi-directional irradiation, like a gamma knife structure, without moving the patient.

Fourth Embodiment

A fourth embodiment of the present invention relates to a charged particle irradiation apparatus 400 in which an imaging unit 420 for viewing a target in the body is added to the charged particle irradiation apparatus 100 of the second embodiment (or the charged particle irradiation apparatus 300 of the third embodiment).

Figure 9:
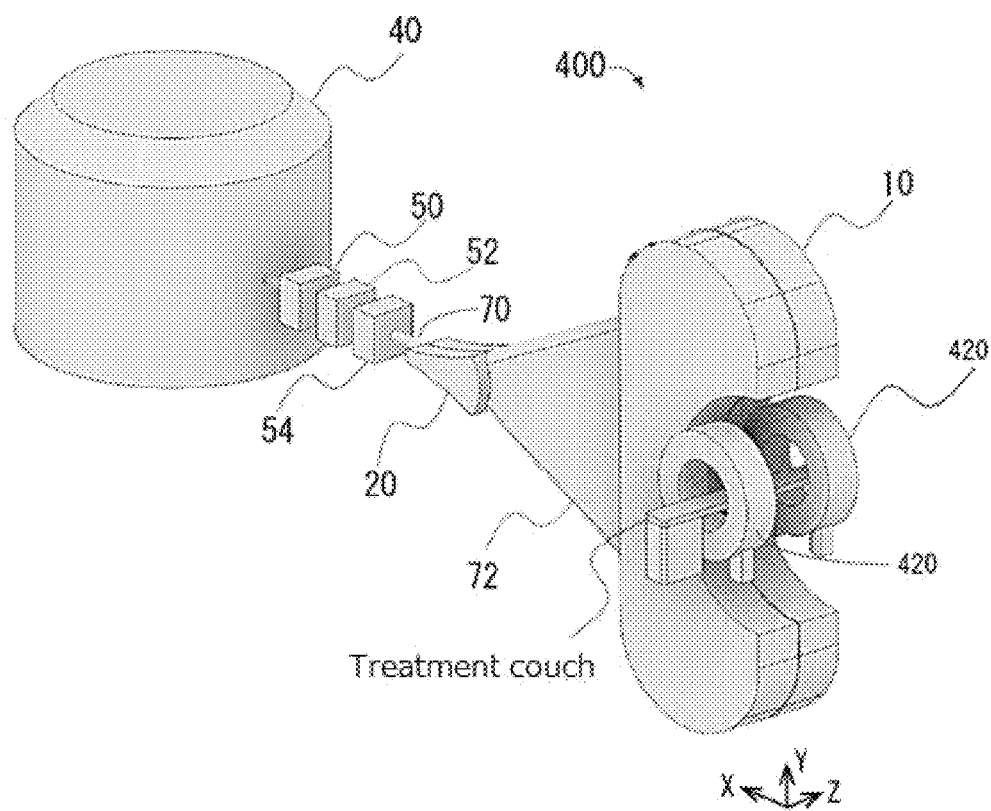
FIG. 9 is a schematic configuration diagram of the charged particle irradiation apparatus of the embodiment.

As shown in FIG. 9, by arranging the imaging unit 420 using an X-ray or MR technique near the patient, the shape of a target (malignant tumor) in the patient can be checked before or during irradiation of the charged particle beam. If the shape of the target in the body can be checked by use of the imaging unit 420 before irradiation of the charged particle beam, the irradiated charged particle beam can be more accurately aligned with the position of the target. Also, the shape (shape of charged particle beam) of a previously planned irradiation area can be fine-adjusted according to the target shape changing over time, on the basis of image information picked up by the imaging unit 420. Moreover, a target may move or deform during irradiation of the charged particle beam. In such a case too, irradiation accuracy can be improved by acquiring image information on the target by use of the imaging unit 420 during irradiation of the charged particle beam, and adjusting the shape of the charged particle beam manually or by the feedback control described in the second embodiment, on the basis of the acquired information.

Fifth Embodiment

A charged particle irradiation apparatus of a fifth embodiment of the present invention will be described with reference to the drawings.

First, in a conventional rotary charged particle irradiation apparatus described in National Publication of International Patent Application No. 2013-505757 or Japanese Patent No. 2836446, although the irradiation angle to the affected area (isocenter) can be varied continuously, the enormous beam transport device needs to be rotated to irradiate the charged particle beam to the isocenter from different directions. Additionally, in a conventional particle therapy system provided with multiple fixed irradiation ports described in Japanese Patent Laid-Open No. 2017-153910, the directions in which the charged particle beam irradiates the isocenter are not continuous, and the same number of beam transport lines as the number of irradiation directions is required. These conventional apparatuses and systems have problems of difficulty in production, manufacturing cost, difficulty in maintenance, and/or installation space.

In view of the foregoing, the embodiment provides a charged particle irradiation apparatus including the focusing magnet 10 (or 200) described in any one of the first to fourth embodiments, and an irradiation nozzle that moves continuously along an exit-side shape of an effective magnetic field region of the focusing magnet 10, in which a charged particle beam exiting from the focusing magnet 10 irradiates an isocenter through the irradiation nozzle.

According to the charged particle irradiation apparatus of the embodiment, the irradiation angle to the isocenter can be varied continuously, and the charged particle beam can irradiate the isocenter continuously from different directions, without rotating an enormous beam transport device or providing the same number of beam transport lines as the number of irradiation directions. This configuration can solve the problems of the conventional apparatus and system related to difficulty in production, manufacturing cost, difficulty in maintenance, and/or installation space.

Figure 10A:
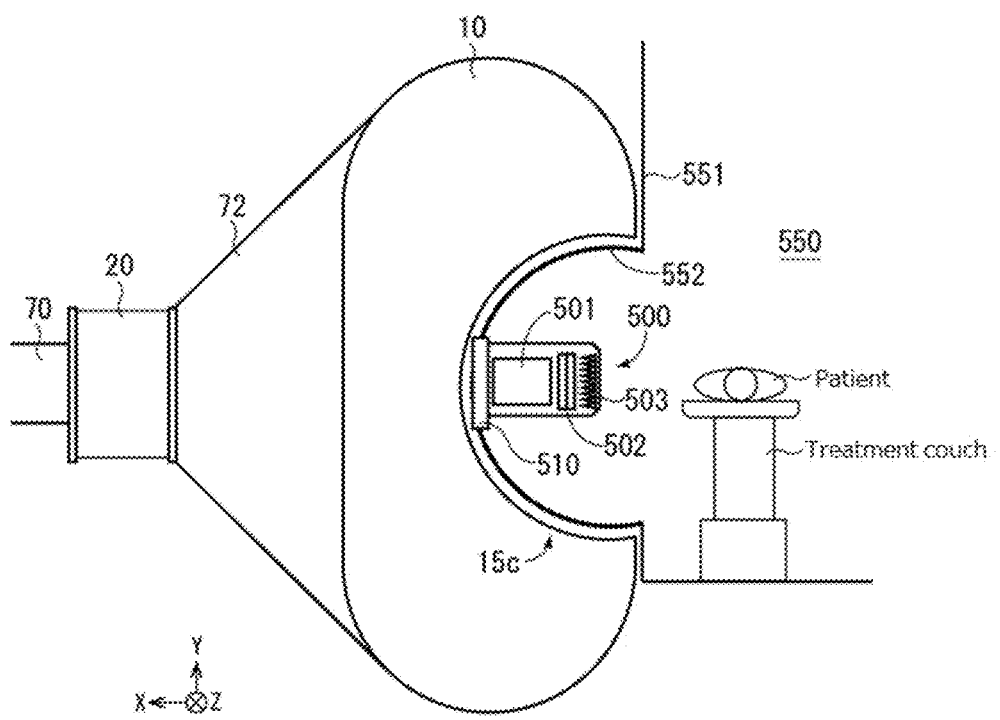
FIG. 10a is a schematic configuration diagram of the charged particle irradiation apparatus of the embodiment.
Figure 10B:
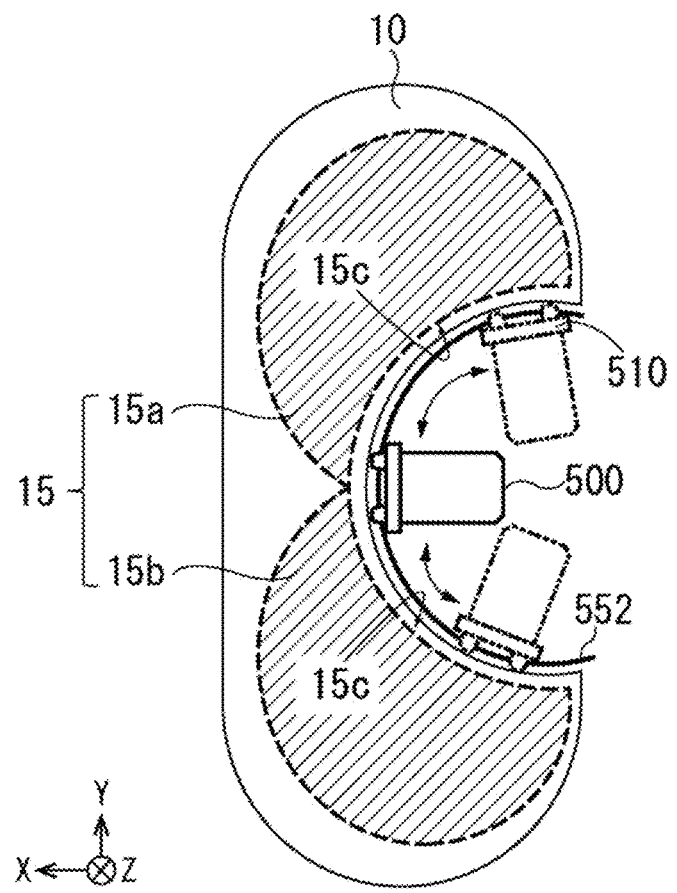
FIG. 10b is a schematic configuration diagram of the charged particle irradiation apparatus of the embodiment.

An irradiation nozzle 500 of the charged particle irradiation apparatus of the embodiment will be described. FIG. 10a is an enlarged schematic diagram of the downstream side of the charged particle irradiation apparatus, that is, a bending magnet unit 20, the focusing magnet 10 (or 200), and the irradiation nozzle 500. FIG. 10b is a schematic diagram showing how the irradiation nozzle 500 moves continuously along the shape (boundary shape) of an exit side 15c of an effective magnetic field region 15 (15a and 15b) on the xy-plane.

The irradiation nozzle 500 is located inside a treatment room 550 in which therapy and the like using a charged particle beam is performed, and is supported by a drive section 510 that moves on a guide rail 552 provided on a wall surface 551 in the treatment room 550. That is, the irradiation nozzle 500 is installed in the treatment room 550 so as to be continuously movable on the guide rail 552.

The guide rail 552 (and wall surface 551 on which guide rail 552 is installed) is preferably provided on the xy-plane along the shape on the exit side 15c of the effective magnetic field region 15 of the focusing magnet 10. In other words, the guide rail 552 is installed such that the irradiation nozzle 500 driven by the drive section 510 can move continuously along the shape on the exit side 15c of the effective magnetic field region 15 of the focusing magnet 10 on the xy-plane.

Moreover, the guide rail 552 may be a cover that forms a part of an inner side of the wall surface 551 of the treatment room 550. The irradiation nozzle 500 may be installed on the cover, and the cover may move continuously along the shape on the exit side 15c of the effective magnetic field region 15 of the focusing magnet 10, so that the irradiation nozzle 500 moves continuously along the shape on the exit side 15c of the effective magnetic field region 15 of the focusing magnet 10. At this time, the irradiation nozzle 500 may be fixed to the cover, or may be configured to move relative to the cover.

The drive section 510 includes a drive motor and a mechanism that moves by driving of the drive motor, for example. When the mechanism moves by being led along the guide rail 552, the irradiation nozzle 500 moves continuously along the shape on the exit side 15c of the effective magnetic field region 15 of the focusing magnet 10.

The charged particle beam exiting from the exit side 15c of the effective magnetic field region 15 of the focusing magnet 10 travels linearly. The irradiation nozzle 500 should preferably be configured such that attenuation of the charged particle beam is most suppressed and adjustment of the charged particle beam in the irradiation nozzle 500 is made easy, when the charged particle beam exiting from the focusing magnet 10 is incident on the center of an incident aperture of the irradiation nozzle 500. Since the irradiation nozzle 500 is moved along the shape on the exit side 15c of the effective magnetic field region 15 on the xy-plane, the charged particle beam exiting from the effective magnetic field region 15 can easily enter the incident aperture of the irradiation nozzle 500, whereby attenuation of the charged particle beam can be avoided or suppressed.

Here, in the charged particle irradiation apparatus of the embodiment, an upstream part from the focusing magnet 10 to the accelerator may be arranged outside the treatment room 550. Additionally, the guide rail 552 may be provided on the focusing magnet 10 along the shape on the exit side 15c of the effective magnetic field region 15 of the focusing magnet 10 on the xy-plane, and install the focusing magnet 10 inside the treatment room 550.

The irradiation nozzle 500 includes a scanning magnet 501, a beam monitor 502, and energy conversion means 503.

The scanning magnet 501 is a magnet for enabling scanning within a predetermined range, by adjusting the amount and direction of current flowing through the scanning magnet 501, and thereby fine-adjusting the traveling direction of the charged particle beam delivered from the irradiation nozzle 500. The beam monitor 502 is a monitor that monitors the charged particle beam, and measures the dose and position, flatness of the beam. The energy conversion means 503 is configured to change the energy of the charged particle beam and to adjust the depth to which the charged particle beam reaches in the patient, and is a range modulator, a scatterer, a ridge filter, a patient collimator, a patient bolus, or an applicator, for example.

Figure 11:
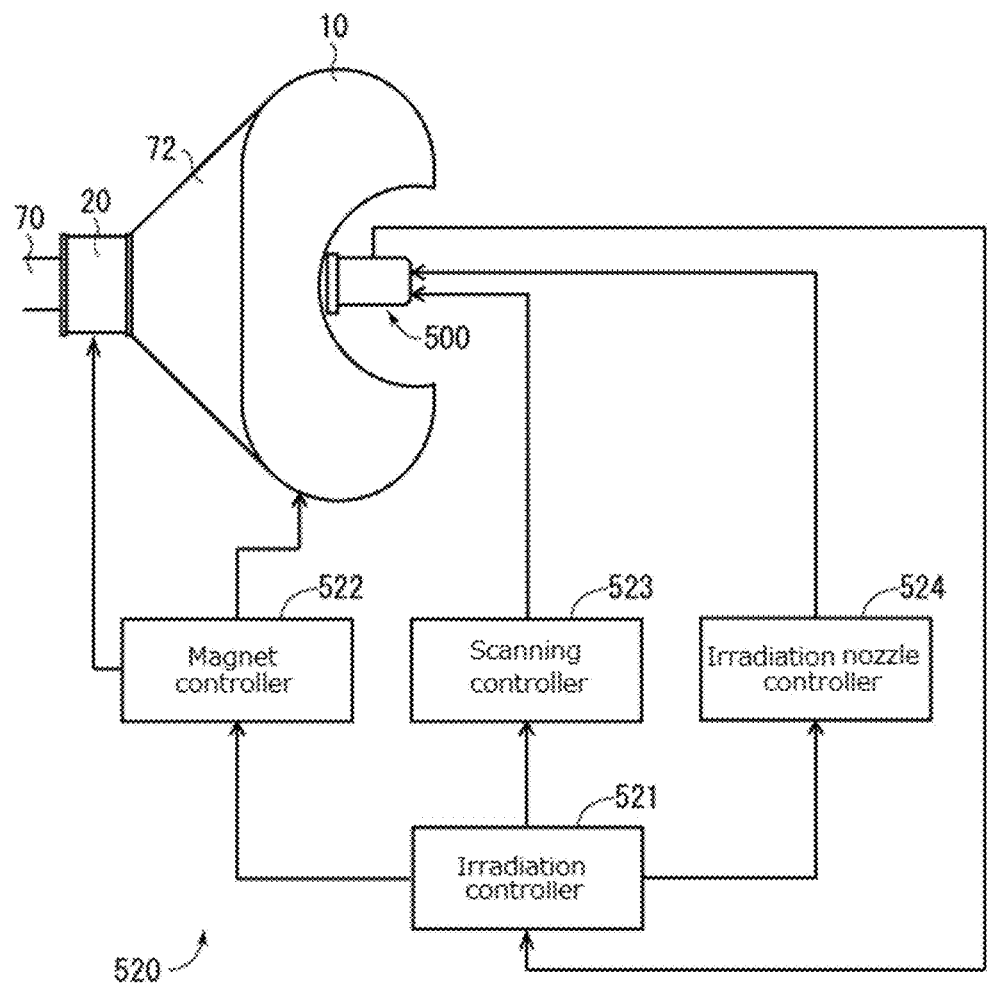
FIG. 11 is a schematic configuration diagram of the charged particle irradiation apparatus of the embodiment.

FIG. 11 is a block diagram related to a control system 520 of the irradiation nozzle 500, the bending magnet unit 20, and the focusing magnet 10. The control system 520 has an irradiation controller 521, a magnet controller 522, a scanning controller 523, and an irradiation nozzle controller 524. The irradiation controller 521 monitors a prescribed dose determined in advance for each target of the charged particle beam irradiation, and controls the magnet controller 522, the scanning controller 523, and the irradiation nozzle controller 524. The magnet controller 522 controls the bending magnet unit 20 and the focusing magnet 10 to adjust the deflection angle $\phi$ and the irradiation angle $\theta$ of the charged particle beam. Note that the magnet controller 522 may control the focusing magnet 10 through an irradiation angle controller 33 (FIG. 3). The scanning controller 523 controls the scanning magnet 501 of the irradiation nozzle 500. Then, the irradiation nozzle controller 524 controls the drive section 510 to control movement of the irradiation nozzle 500.

Figure 12:
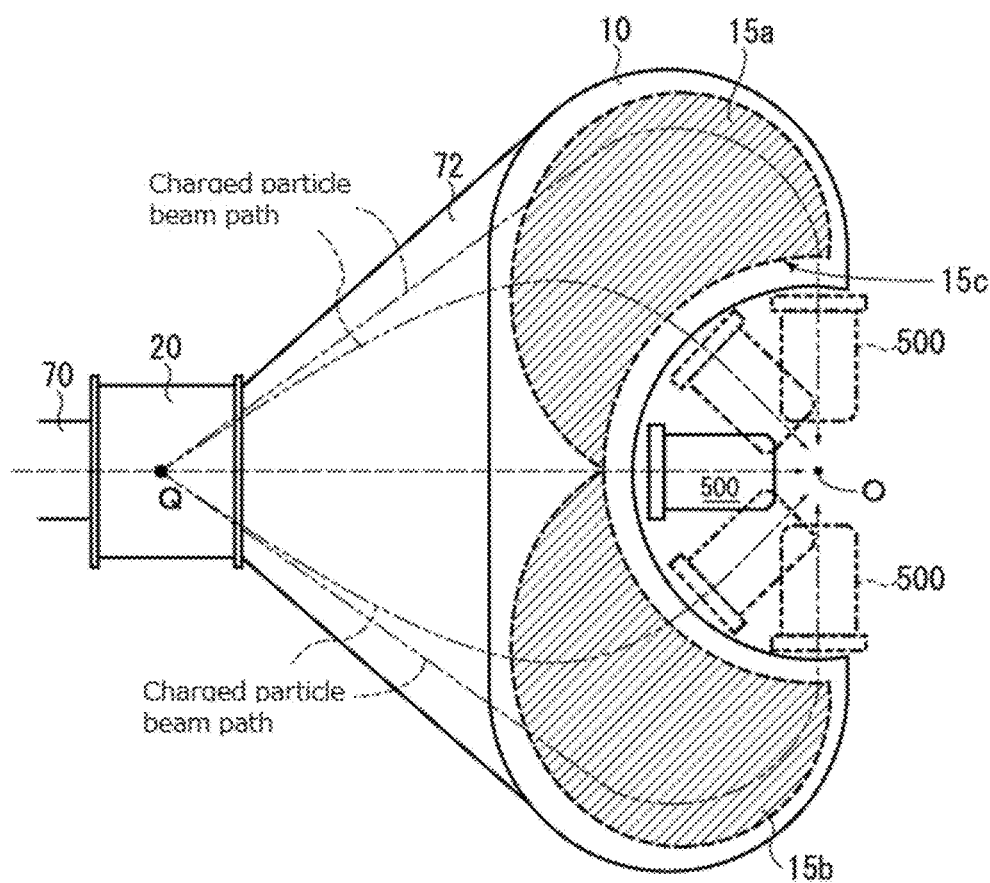
FIG. 12 is a schematic configuration diagram of the charged particle irradiation apparatus of the embodiment.

The irradiation controller 521 transmits instructions to the magnet controller 522 and the irradiation nozzle controller 524, according to a preset direction (irradiation angle θ) of the charged particle beam to irradiate the affected part (isocenter). Upon receipt of the instruction, the magnet controller 522 adjusts the current applied to the bending magnet unit 20 and/or the focusing magnet 10, so that the irradiation angle θ of the charged particle beam exiting from the focusing magnet 10 is a preset irradiation angle. Additionally, upon receipt of the instruction from the irradiation controller 521, the irradiation nozzle controller 524 drives the drive section 510 so that the charged particle beam exiting from the focusing magnet 10 passes through an incident aperture's center of the irradiation nozzle 500 before starting irradiation of the charged particle beam, and continuously moves the irradiation nozzle 500 (FIG. 12).

While irradiating the charged particle beam to the affected part, the irradiation controller 521 may receive information (such as position, width, and dose of charged particle beam) from the beam monitor 502 of the irradiation nozzle 500, determine whether the irradiation of the charged particle beam on the affected part is appropriate, and perform feedback control. For example, when the irradiation controller 521 determines, on the basis of information from the beam monitor 502, that the direction (irradiation angle θ) of the charged particle beam is inappropriate as compared to the direction of the charged particle beam preset for the affected part, the magnet controller 522 and/or the scanning controller 523 are controlled to fine-adjust the irradiation angle θ, and/or the charged particle beam is scanned and adjusted within a predetermined angle range from the irradiation angle θ. When the irradiation controller 521 determines that the irradiation amount of the charged particle beam is not appropriate as compared to a value preset for the affected part, the irradiation nozzle controller 524 may control the energy conversion means 503 of the irradiation nozzle 500, and adjust the irradiation amount of the charged particle beam on the affected part.

As has been described, the charged particle irradiation apparatus of the embodiment includes: the focusing magnet 10 capable of continuously varying the irradiation angle θ on the affected part; and the irradiation nozzle 500 capable of continuously moving along the shape on the exit side 15c of the effective magnetic field region 15 of the focusing magnet 10 on the xy-plane, and can irradiate the charged particle beam to the affected part continuously from arbitrary directions. Additionally, when a conventional rotary irradiation apparatus is used, the apparatus and installed facility need to be large, which may cause problems such as difficulty in production, manufacturing cost, difficulty in maintenance, and/or installation space; however, the charged particle irradiation apparatus of the embodiment can solve these problems. Moreover, in the conventional irradiation apparatus, although a once installed irradiation nozzle is difficult to move, and a test period is required to perform fine-adjustment of the nozzle position in some cases, the charged particle irradiation apparatus of the embodiment can also solve this problem.

To maintain a high irradiation accuracy, the irradiation angle θ of the charged particle beam irradiating the affected part (isocenter) should preferably be controlled with high precision. However, the accuracy of the irradiation angle θ may decrease if deviation in the trajectory of the charged particle beam, variation in the shape of the charged particle beam (state of charged particle beam), and the like are not within an allowable value due to an alignment error of various units of the charged particle irradiation apparatus, or error in the magnetic field of various magnets. A conventional apparatus (Japanese Patent Laid-Open No. 2017-153910) is configured such that an irradiation nozzle moves to a certain transport line according to the irradiation direction (horizontal, 45 degrees, and vertical). However, in this configuration, since the distance from an exit of a focusing magnet to an irradiation point also changes depending on the irradiation direction, a magnet for correcting the change in distance needs to be placed separately from the irradiation nozzle on the downstream side of the focusing magnet. The charged particle irradiation apparatus of the embodiment can solve this problem. Additionally, in the charged particle irradiation apparatus of the embodiment, error in alignment of various magnets in the transport system of the charged particle beam can be absorbed (adjusted) in the position of the irradiation nozzle 500, and therefore the commissioning period for adjustment can be reduced.

(Another Aspect)

Figure 13:
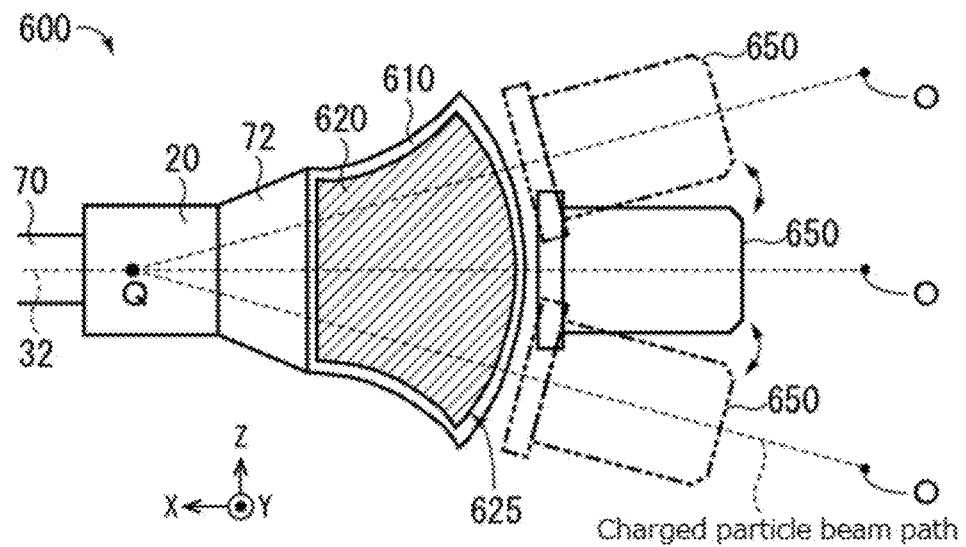
FIG. 13 is a schematic diagram of a charged particle irradiation apparatus of another embodiment.

Another aspect relates to a charged particle irradiation apparatus 600 (FIG. 13) including a focusing magnet 610 that can continuously deflect a charged particle beam on an xz-plane perpendicular to an xy-plane, and an irradiation nozzle 650 that can move continuously along an exit side-shape of an effective magnetic field region 620 of the focusing magnet 610.

The charged particle irradiation apparatus 600 of the embodiment is configured to continuously drive the irradiation nozzle 650 within a horizontal plane (xz-plane). Although there are multiple irradiation points (isocenter O) in the embodiment, the irradiation nozzle 650 can continuously move along the shape on an exit side 625 (on the xz-plane) of the effective magnetic field region 620 of the focusing magnet 610. Hence, no additional magnet needs to correct the charged particle beam between the focusing magnet 610 and the irradiation nozzle 650. Moreover, since the irradiation nozzle 650 can continuously move along the shape on the exit side 625 (on the xz-plane) of the effective magnetic field region 620 of the focusing magnet 610, error in alignment of various magnets can be absorbed (adjusted) in the position of the irradiation nozzle 650, and therefore the commissioning period can be reduced.

The dimensions, materials, shapes, and relative positions or the like of components described in the above embodiments are varied according to the structure or various conditions of the apparatus to which the present invention is applied. Specific terms and embodiments used in the description are not intended for limitation, and a person skilled in the art would easily arrive at use of other equivalent components. The above embodiment may be modified or varied within the gist and scope of the present invention. Additionally, a characteristic described in relation to one embodiment of the invention is usable in combination with another embodiment, even if not clearly specified.

REFERENCE SIGNS LIST 10, 200 focusing magnet
11a, 11b coil pair
12a, 12b magnetic pole
13 yoke
15, 15a, 15b effective magnetic field region
15c exit side of effective magnetic field region
16 incident side of charged particle beam
17 exit side of charged particle beam
18 bus bar
20 bending magnet unit
30 power supply unit
31 selector unit
32 power supply 33 irradiation angle controller
40 accelerator
50 beam slit unit
52 quadrupole magnet unit
54 steering magnet unit
60 beam monitor unit
70, 72 vacuum duct
100, 300, 400 charged particle irradiation apparatus
220 drive unit
420 imaging unit
500 irradiation nozzle
510 drive section

What is claimed is:

1. A charged particle irradiation apparatus comprising:
a focusing magnet; and
an irradiation nozzle that moves continuously along the shape on an exit side of an effective magnetic field region of the focusing magnet, wherein
the charged particle beam exiting from the focusing magnet irradiates the isocenter through the irradiation nozzle, wherein
the focusing magnet comprises a coil pair arranged on both sides of a path of a charged particle beam, wherein:
when a current is input, the coil pair is configured to generate an effective magnetic field region in which a magnetic field is oriented in a direction (z-axis) perpendicular to a traveling direction (x-axis) of a charged particle beam, where an axis perpendicular to the x-axis and z-axis is assumed to be a y-axis;
in an xy-plane,
a charged particle beam which has been deflected at a deflection angle $\phi$ with respect to the x-axis at a deflection point Q and incident on the effective magnetic field region is deflected by the effective magnetic field region, and irradiates an isocenter at an irradiation angle $\theta$ with respect to the x-axis,
an arbitrary point P2 on a boundary on an exit side of the charged particle beam of the effective magnetic field region is at an equal distance $r_1$ from the isocenter,
a point P1 on a boundary on an incident side of the charged particle beam of the effective magnetic field region and the point P2 are on a radius $r_2$ and an arc of a central angle $(\theta+\phi)$, and
when a distance between the deflection point Q and the isocenter is L, a distance R between the deflection point Q and the point P1 satisfies the following relational equation (4):

$$R=\sqrt{L^2+r_1^2-2L(r_1\cos\theta+r_2\sin\theta)} \qquad (4)$$

2. The charged particle irradiation apparatus according to claim 1, wherein:
the irradiation nozzle includes a scanning magnet that enables scanning of the charged particle beam within a predetermined range, and a beam monitor that monitors the charged particle beam; and
the charged particle irradiation apparatus further comprises a scanning controller that controls the scanning magnet to scan the charged particle beam, on the basis of information from the beam monitor.

3. The charged particle irradiation apparatus according to claim 2, wherein:
(i) the irradiation nozzle moves on a guide rail provided along the shape on an exit side of an effective magnetic field region of the focusing magnet, or
(ii) the irradiation nozzle is installed on a cover forming a part of the inner side of a wall surface of a treatment room, and when the cover moves continuously along the shape of the exit side of the effective magnetic field region of the focusing magnet, the irradiation nozzle moves continuously along the shape on the exit side of the effective magnetic field region of the focusing magnet.

4. A charged particle irradiation apparatus comprising:
a focusing magnet that deflects a charged particle beam to continuously vary an irradiation angle of the charged particle beam on an isocenter; and
an irradiation nozzle that moves continuously along the shape on an exit side of an effective magnetic field region of the focusing magnet, wherein
the charged particle beam exiting from the focusing magnet irradiates the isocenter through the irradiation nozzle.

* * * * *